(12) United States Patent
Antons et al.

(10) Patent No.: US 11,618,735 B2
(45) Date of Patent: Apr. 4, 2023

(54) CRYSTAL FORMS OF THE MONOSODIUM SALT OF FORAMSULFURON

(71) Applicant: Bayer CropScience Aktiengesellschaft, Monheim am Rhein (DE)

(72) Inventors: Stefan Antons, Leverkusen (DE); Britta Olenik, Bottrop (DE); Martin Krueger, Muecke (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 524 days.

(21) Appl. No.: 16/538,972

(22) Filed: Aug. 13, 2019

(65) Prior Publication Data

US 2019/0389813 A1     Dec. 26, 2019

Related U.S. Application Data

(62) Division of application No. 15/535,310, filed as application No. PCT/EP2015/079283 on Dec. 10, 2015, now Pat. No. 10,472,331.

(30) Foreign Application Priority Data

Dec. 15, 2014 (EP) .................................. 14198010

(51) Int. Cl.
 *C07D 239/52* (2006.01)
 *A01N 47/36* (2006.01)

(52) U.S. Cl.
 CPC ........... *C07D 239/52* (2013.01); *A01N 47/36* (2013.01); *C07B 2200/13* (2013.01)

(58) Field of Classification Search
 None
 See application file for complete search history.

(56) References Cited

U.S. PATENT DOCUMENTS

| 9,475,765 B2 ‡ | 10/2016 | Jones | A01N 47/30 |
| 10,015,967 B2 ‡ | 7/2018 | Bristow | A01N 47/36 |
| 10,059,676 B2 ‡ | 8/2018 | Bristow | A01N 47/36 |
| 2015/0031877 A1 ‡ | 1/2015 | Hiratsuka | A01N 43/84 544/105 |

FOREIGN PATENT DOCUMENTS

| EP | 1902618 A1 ‡ | 3/2008 | ........... C07D 409/12 |
| EP | 1902618 A1 | 3/2008 | |
| WO | 9529899 A1 | 11/1995 | |
| WO | WO-9529899 A1 ‡ | 11/1995 | ............. A01N 47/36 |

OTHER PUBLICATIONS

McClurg, R.B., "X-Ray Powder Diffraction (XRPD) to Describe Crystal Forms," Publication of SSCI an Aptuit Company, Jul. 9, 2008, pp. 1-23.*

* cited by examiner
‡ imported from a related application

*Primary Examiner* — John Pak
(74) *Attorney, Agent, or Firm* — McBee Moore & Vanik IP, LLC

(57) ABSTRACT

The present invention relates to a novel crystal form of the monosodium salt of foramsulfuron, a method for preparing this crystal form, use thereof in agrochemical formulations and also particular compositions, mixtures or agrochemical formulations comprising this crystal form, and also a novel monomethanol solvate of the monosodium salt of foramsulfuron.

8 Claims, 3 Drawing Sheets

CRYSTAL FORMS OF THE MONOSODIUM SALT OF FORAMSULFURON

CROSS-REFERENCE TO RELATED APPLICATIONS

This application is a Divisional Application of U.S. application Ser. No. 15/535,310, filed on 21 Sep. 2017, which is a National Stage entry of International Application No. PCT/EP2015/079283, filed 10 Dec. 2015, which claims priority to European Patent Application No. 14198010.2, filed 15 Dec. 2014. The disclosure of the priority applications are incorporated in their entirety herein by reference.

BACKGROUND

Field

The present invention relates to a novel crystal form of the monosodium salt of foramsulfuron, a method for preparing this crystal form, use thereof in agrochemical formulations and also particular compositions, mixtures or agrochemical formulations comprising this crystal form, and also a novel monomethanol solvate of the monosodium salt of foramsulfuron.

Description of Related Art

Foramsulfuron of formula (I) below and the monosodium salt thereof are known from EP 0 757 679 A1.

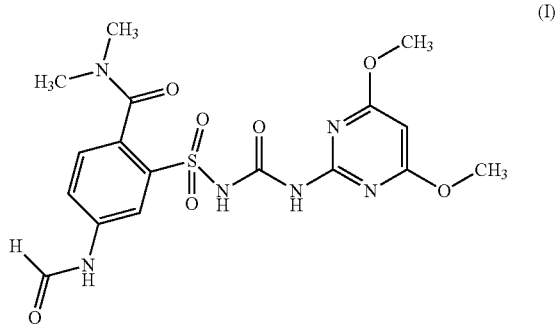 [SMILES: COc1cc(OC)nc(NC(=O)NS(=O)(=O)c2cc(NC=O)ccc2C(=O)N(C)C)n1]

Foramsulfuron of formula (I) and certain salts of this compound are known herbicidal active ingredients, see "The Pesticide Manual", 16th edition, The British Crop Protection Council and the Royal Society of Chemistry, 2012.

It is also known that foramsulfuron of formula (I) and salts thereof may be used in combination with other herbicidal active ingredients and/or with safeners, described in EP 0 790 771 A1 or EP 1 104 239 A1 for example.

Foramsulfuron has the empirical formula $C_{17}H_{20}N_6O_7S$, CAS number 173159-57-4 and IUPAC name 1-(4,6-dimethoxypyrimidin-2-yl)-3-[2-(dimethylcarbamoyl)-5-formamidophenylsulphonyl]urea, and is also referred to below as N-[(4,6-dimethoxypyridin-2-yl)aminocarbonyl]-2-dimethylaminocarbonyl-5-formylaminobenzenesulphonamide.

The compound of formula (I) and the monosodium salt thereof can be prepared by the methods described in EP 0 757 679 A1 and U.S. Pat. No. 6,500,952 B1.

EP 1 902 618 A1 describes methods for preparing sulphonamide salts.

Only one crystal form of the monosodium salt of foramsulfuron has been known to date, which is referred to hereinafter as crystal form A. This crystal form A corresponds to a semi-methanol solvate.

The crystal lattice of a solid can be made up of several chemical components. If one of these is a liquid (e.g. a solvent), these are termed solvates.

The occurrence of active ingredients in various crystalline modifications (polymorphs) is of great significance both for the development of production processes and for the development of formulations (agrochemical formulations). For instance, the different crystalline modifications of a chemical compound differ not only in appearance (crystal habit) and hardness, but also in numerous further physicochemical properties. Differences in terms of stability, filterability, solubility, hygroscopicity, melting point, solid density and flowability can exert a strong influence on the quality and the efficacy of plant treatment compositions. It has not been possible to date to predict the occurrence and number of crystalline modifications, including the physicochemical properties thereof. In particular, the thermodynamic stability and also the different behaviour after administration to living organisms cannot be predicted. The above embodiments, referring to polymorphs, are applicable analogously to pseudopolymorphs.

The known crystal form A has some disadvantageous properties which are briefly described below.

Crystal form A may have a disadvantageous effect on the stability or storability of compositions (e.g. agrochemical formulations) comprising crystal form A. This may be the case because, for example, the chemical stability of crystal form A in certain compositions is not sufficient and/or further constituents (e.g. other active ingredients) of these compositions are negatively influenced in terms of their chemical stability by crystal form A, and their content in the composition decreases with time. It may also occur that a composition (e.g. agrochemical formulation) comprising crystal form A is unstable over a long (storage) period, and the physical properties of the composition changes, for example, the viscosity or flowability of the composition changes in an undesirable manner.

It is also known that sulphonylurea herbicides are subjected to chemical degradation reactions in the presence of particular auxiliaries, such as alcoholic diluents, particularly methanol, which leads to a decrease in the active ingredient content of the sulphonylurea herbicide over long storage periods, which is undesirable. This chemical degradation also occurs in compositions (such as mixtures or formulations) comprising foramsulfuron and salts thereof in combination with other sulphonylurea herbicides or salts thereof, for example, in compositions described in EP 1 104 239 A1. This applies in particular to readily chemically degradable/hydrolysable sulphonylurea herbicides such as iodosulfuron, iodosulfuron-methyl and respective salts thereof such as iodosulfuron-sodium or iodosulfuron-methyl-sodium.

In some cases, furthermore, the technical handling of the known crystal form A is difficult. For instance, according to the preparation method described in EP 0 757 679 A1, this crystal form A occurs in the form of flocculent and poorly filterable aggregates.

SUMMARY

The object of the invention, therefore, is to remedy one, several or all of the disadvantage(s) mentioned above in connection with the known crystal form A or to improve the disadvantageous properties mentioned above in connection with the known crystal form A.

This object is achieved in accordance with the invention by a novel crystal form of the monosodium salt of the compound of formula (I) having the empirical formula $C_{17}H_{19}N_6O_7SNa$, which is referred to hereinafter as crystal form B.

Therefore, the invention primarily relates to the monosodium salt of foramsulfuron in crystalline form (crystal form B), characterized in that the X-ray powder diffractogram of this salt using Cu Kα radiation at 25° C. has at least 3 of the following 2Θ (2 theta) values:

| 2Θ (2 theta) values in ° |
| --- |
| 6.2 |
| 6.4 |
| 14.4 |
| 14.6 |
| 14.7 |
| 18.4 |
| 19.2 |
| 20.1 |
| 23.2 |
| 24.7 |

This inventive crystal form B is characterized in that it has an X-ray powder diffractogram having the 2Θ (2 theta) reflections reported in Table 1. The X-ray powder diffractogram of crystal form B is also shown in FIG. 2. The most intensive and characteristic 2Θ (2 theta) signals in the X-ray powder diffractogram of crystal form B are at 6.2, 6.4, 14.4, 14.6, 14.7, 18.4, 19.2, 20.1, 23.2, and 24.7° (in each case±0.2°).

The inventive crystal form B is characterized in that the X-ray powder diffractogram of this salt using Cu Kα radiation at 25° C. has at least 4, preferably at least 5, preferably at least 6, more preferably at least 7, particularly preferably at least 8 and especially preferably all of the most intensive 2Θ (2 theta) signals specified above.

The inventive crystal form B is preferably characterized in that the X-ray powder diffractogram of this salt using Cu Kα radiation at 25° C. additionally has at least two, four, six, eight, ten, twelve or more, preferably at least 15, 20, 23, 25, 27, 30, 33, 35, 38, 40, 42, 44, 46, 48, 50 or more, preferably all of the following 2Θ (2 theta) values:

| |
| --- |
| 10.3 |
| 10.5 |
| 11.1 |
| 11.3 |
| 11.4 |
| 12.0 |
| 12.1 |
| 12.4 |
| 12.6 |
| 12.9 |
| 13.6 |
| 14.0 |
| 15.0 |
| 15.1 |
| 15.4 |
| 16.0 |
| 16.2 |
| 17.0 |
| 17.2 |
| 18.2 |
| 18.8 |
| 20.3 |
| 20.6 |
| 20.8 |
| 21.2 |
| 21.6 |
| 22.7 |
| 23.7 |
| 24.6 |
| 25.4 |
| 25.9 |
| 26.2 |
| 26.9 |
| 27.1 |
| 27.7 |
| 28.3 |
| 29.0 |
| 30.2 |
| 30.5 |
| 30.7 |
| 31.0 |
| 31.2 |
| 31.9 |
| 32.5 |
| 32.6 |
| 33.7 |
| 34.8 |
| 35.6 |
| 35.9 |
| 36.2 |
| 36.4 |
| 36.9 |
| 37.4 |

BRIEF DESCRIPTION OF THE DRAWINGS

The X-ray powder diffractogram of crystal form A is shown in FIG. 1.

The X-ray powder diffractogram of crystal form B is shown in FIG. 2.

Figure 3:
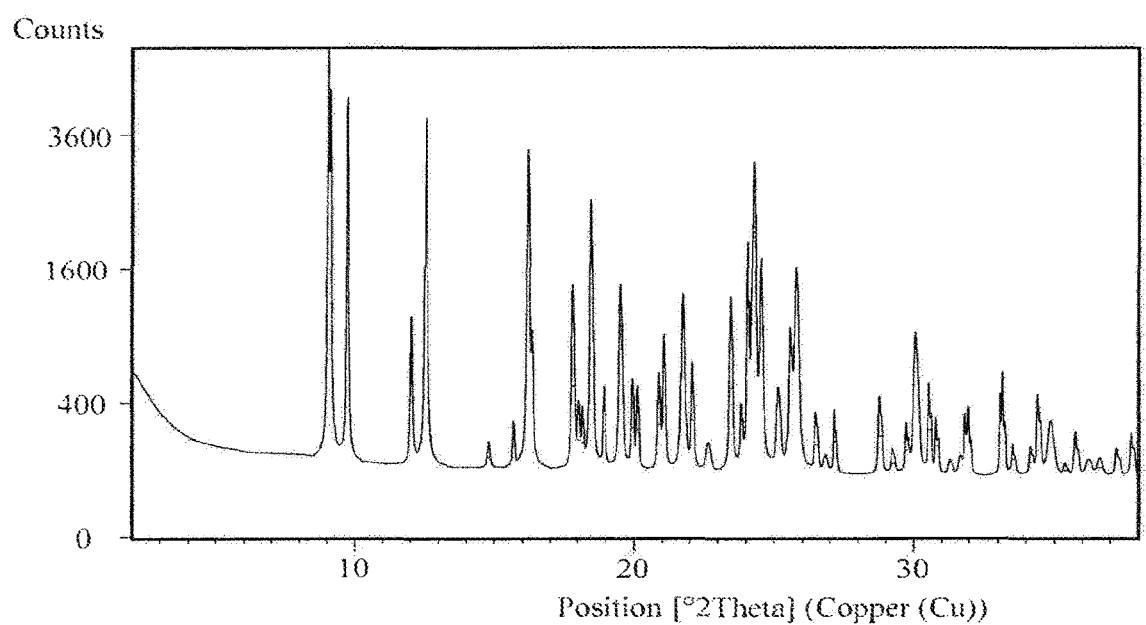

The X-ray powder diffractogram of crystal form C is shown in FIG. 3.

Figure 4:
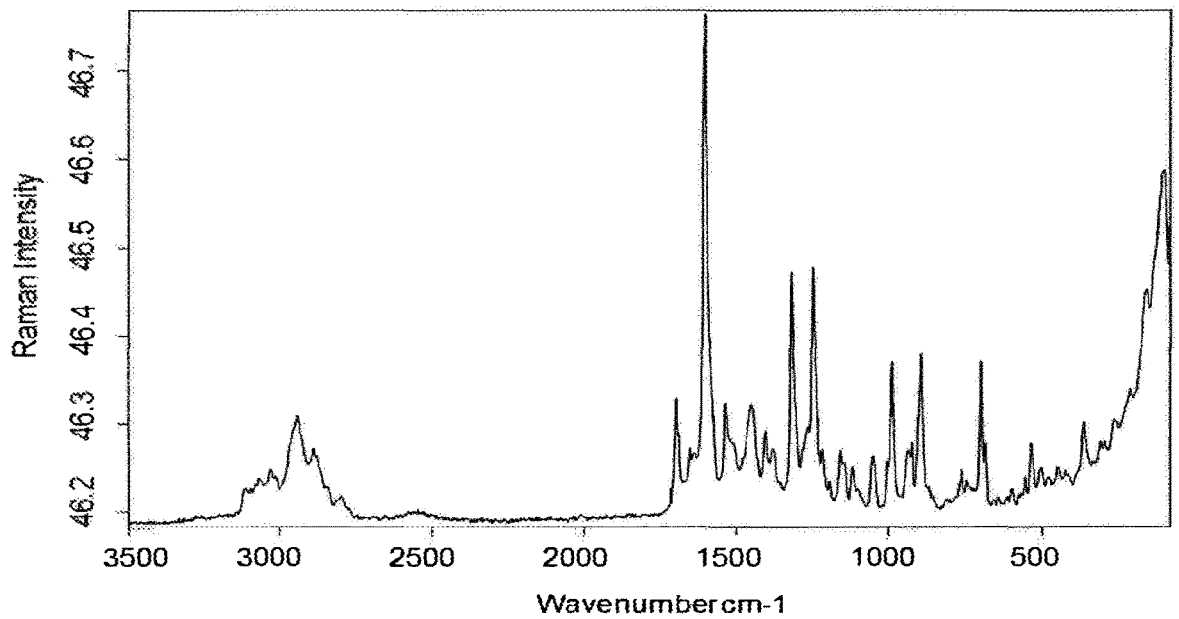

The Raman spectrum of crystal form A is shown in FIG. 4.

Figure 5:
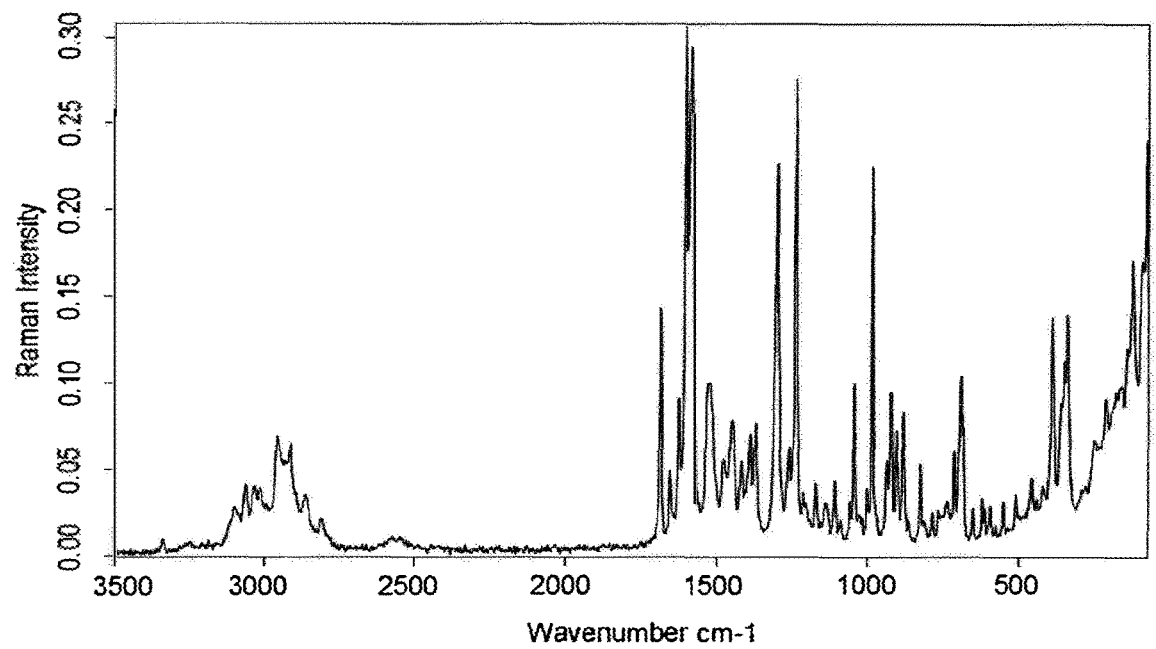

The Raman spectrum of crystal form B is shown in FIG. 5.

Figure 6:
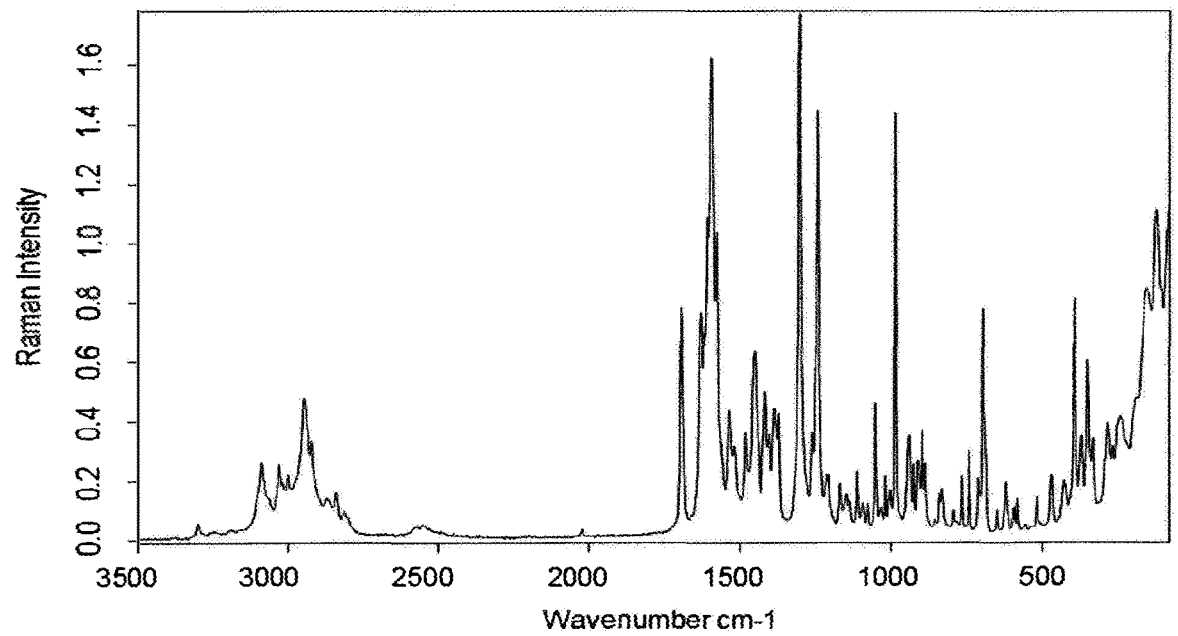

The Raman spectrum of crystal form C is shown in FIG. 6.

DETAILED DESCRIPTION OF A PREFERRED EMBODIMENT

The inventive crystal form B, unlike crystal form C described below, is non-hygroscopic and has improved stability in formulations (agrochemical formulations).

The inventive crystal form B is better suited to the preparation of (storage) stable formulations and it is more compatible with other sulphonylurea herbicides and salts thereof, particularly with iodosulfuron and salts thereof, since sulphonylurea herbicides (in particular here iodosulfuron) and salts thereof have unsatisfactory stability, particularly unsatisfactory chemical stability, in mixtures with crystal form A.

All X-ray powder diffractometry data stated in the present text refers to the following measurement parameters:

| | |
| --- | --- |
| Scan axis | gonio |
| Scan Mode | transmission |
| Start Position [°2theta] | 2.0066 |
| End Position [°2theta] | 37.9906 |
| Anode material | Cu |
| Wavelength K-alpha1 [Å] | 1.54060 |
| Wavelength K-alpha2 [Å] | 1.54443 |
| Wavelength K-beta [Å] | 1.39225 |

-continued

| | |
|---|---|
| K-A2/K-A1 ratio | 0.50000 |
| Generator | 40 mA, 40 kV |
| Incident Beam Monochromator | focusing X-ray mirror |
| Spinning | yes |
| 2Θ (2 theta) values | ±0.2° |

Furthermore, in the context of the present invention, the crystalline form referred to below as crystal form C was found. It takes the form of the monomethanol solvate of the monosodium salt of the compound of formula (I). Crystal form C may be obtained, for example, when crystal form A is stored over a long time period with methanol, which changes crystal form A into crystal form C. Crystal form C is described in further detail below.

Crystal forms A, B and C are characterized by different X-ray powder diffractograms. In Table 1 below, the respective most intensive characteristic 2Θ (2 theta) reflections are stated, while Table 3 further below shows all 2Θ (2 theta) reflections.

TABLE 1

Characteristic reflections-X-ray diffractometry of
crystal forms A, B and C (as defined above)
Peak maximum [2 theta], data in °

| Crystal form A | Crystal form B | Crystal form C |
|---|---|---|
| 7.4 | 6.2 | 9.1 |
| 8.7 | 6.4 | 9.1 |
| 9.0 | 14.4 | 9.7 |
| 9.2 | 14.6 | 12.6 |
| 9.3 | 14.7 | 16.2 |
| 15.7 | 18.4 | 18.5 |
| 23.3 | 19.2 | 24.1 |
| 23.3 | 20.1 | 24.3 |
| 23.6 | 23.2 | 24.6 |
| 26.0 | 24.7 | |

If the 2Θ (2 theta) reflections of the X-ray powder diffractogram specified in the present text for a given crystalline form have the same value twice (for example the 2Θ peak maximum at 23.3° in the case of crystal form A), this takes the form of two closely spaced peaks. Due to rounding of the measurement value of the respective peak maximum to one decimal place, two peaks with the same value can arise, but which actually take the form of two peaks in the X-ray powder diffractogram.

Figure 1:
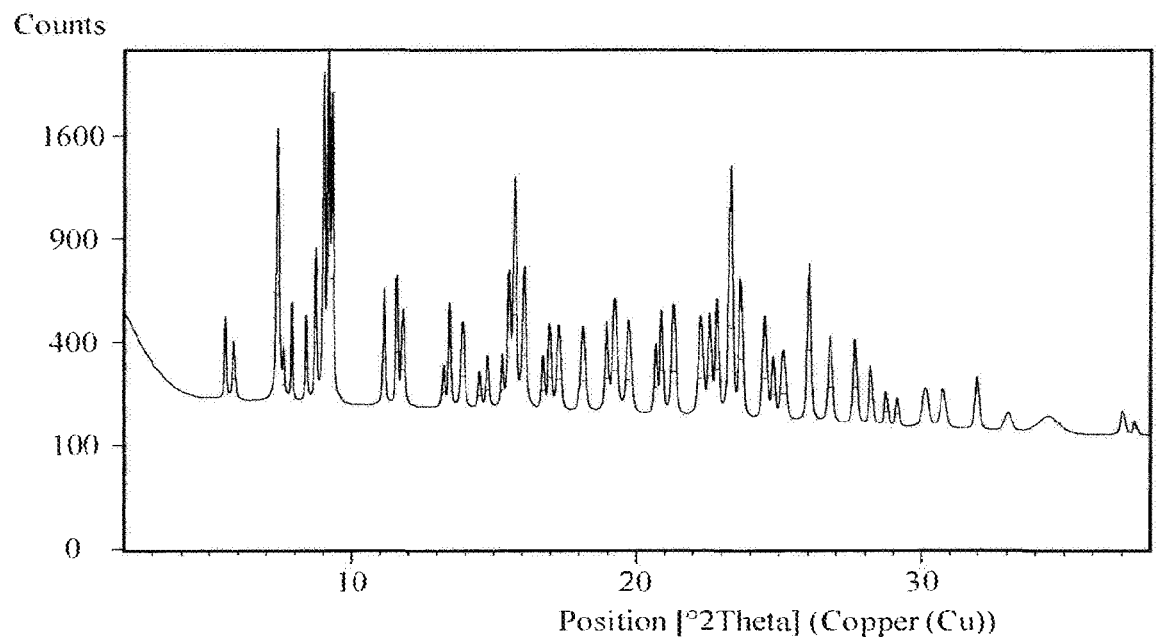
Figure 2:
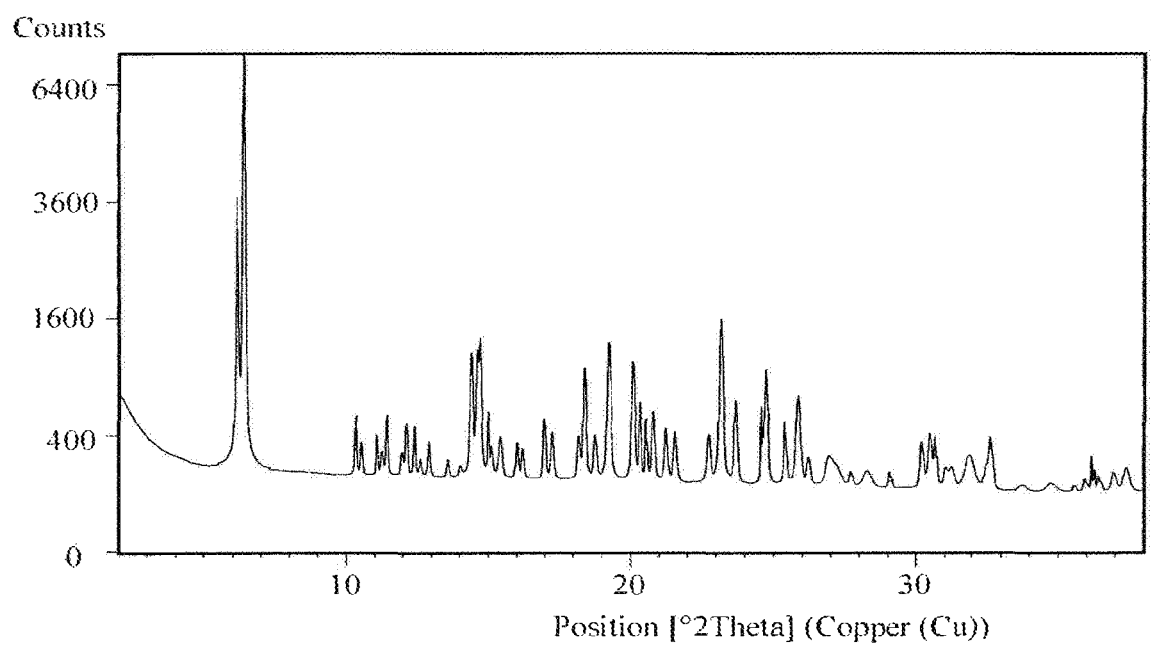

The inventive monosodium salt of foramsulfuron in crystalline form is particularly preferably characterized in that the X-ray powder diffractogram using Cu Kα radiation at 25° C. corresponds essentially to the spectrum shown in FIG. 2.

Crystal forms A, B and C are characterized by Raman spectra. In Table 2 below, the most intensive, characteristic bands are given in each case.

All Raman spectroscopy data given in the present text refer to the following measurement parameters, in which the position of the band maxima of the wave number are in each case stated in cm$^{-1}$:

| | |
|---|---|
| Instrument | Bruker Raman RFS 100/S |
| Number of scans | 64 |
| Resolution | 2-4 cm$^{-1}$ |
| Laser power | 50 mW |
| Laser wavelength | 1064 nm |

Inventive crystal form B is preferably characterized in that the Raman spectrum thereof has at least the following bands:

| Band maximum [cm$^{-1}$] |
|---|
| 2959 |
| 2915 |
| 1686 |
| 1587 |
| 1526 |
| 694 |
| 345 |
| 133 |

The Raman spectrum of crystal form B according to the invention preferably has at least ten of the bands specified in Table 4 below, preferably 15, 20, 25, 30, 35, 40, 45, 50, 55, 60, 65 or more, preferably all of the bands specified in Table 4 below.

TABLE 2

Characteristic bands of the Raman spectra of
crystal forms A, B and C (as defined above)
Band maximum [cm$^{-1}$]

| Crystal form A | Crystal form B | Crystal form C |
|---|---|---|
| 2941 | 2959 | 3090 |
| 1700 | 2915 | 2943 |
| 1320 | 1686 | 2919 |
| 1250 | 1587 | 1593 |
| 990 | 1526 | 1576 |
| 697 | 694 | 691 |
| 362 | 345 | 156 |
| 103 | 133 | 122 |

The Raman spectrum of inventive crystal form B preferably corresponds essentially to the spectrum shown in FIG. 5.

TABLE 3

X-ray diffractometry of crystal forms A, B and C (as defined above)
Peak maximum [2 theta]

| Crystal form A | Crystal form B | Crystal form C |
|---|---|---|
| 5.6 | 6.2 | 9.1 |
| 5.9 | 6.4 | 9.1 |
| 7.4 | 10.3 | 9.7 |
| 7.6 | 10.5 | 12.0 |
| 7.9 | 11.1 | 12.6 |
| 8.4 | 11.3 | 14.8 |
| 8.7 | 11.4 | 15.7 |
| 9.0 | 12.0 | 16.2 |
| 9.2 | 12.1 | 16.3 |
| 9.3 | 12.4 | 17.8 |
| 11.1 | 12.6 | 18.0 |
| 11.6 | 12.9 | 18.2 |
| 11.8 | 13.6 | 18.5 |
| 13.2 | 14.0 | 19.0 |
| 13.4 | 14.4 | 19.5 |
| 13.9 | 14.6 | 19.9 |
| 14.5 | 14.7 | 20.1 |
| 14.8 | 15.0 | 20.9 |
| 15.3 | 15.1 | 21.1 |
| 15.5 | 15.4 | 21.7 |
| 15.7 | 16.0 | 22.1 |
| 16.1 | 16.2 | 22.6 |
| 16.7 | 17.0 | 23.5 |
| 17.0 | 17.2 | 23.8 |
| 17.3 | 18.2 | 24.1 |
| 18.1 | 18.4 | 24.3 |
| 19.0 | 18.8 | 24.5 |

TABLE 3-continued

X-ray diffractometry of crystal forms A, B and C (as defined above)
Peak maximum [2 theta]

| Crystal form A | Crystal form B | Crystal form C |
|---|---|---|
| 19.2 | 19.2 | 24.6 |
| 19.7 | 20.1 | 25.1 |
| 20.7 | 20.3 | 25.6 |
| 20.9 | 20.6 | 25.8 |
| 21.3 | 20.8 | 26.5 |
| 22.3 | 21.2 | 26.8 |
| 22.6 | 21.6 | 27.1 |
| 22.8 | 22.7 | 28.8 |
| 23.3 | 23.2 | 29.2 |
| 23.3 | 23.7 | 29.7 |
| 23.6 | 24.6 | 30.0 |
| 24.5 | 24.7 | 30.5 |
| 24.8 | 25.4 | 30.8 |
| 25.1 | 25.9 | 31.3 |
| 26.0 | 26.2 | 31.7 |
| 26.8 | 26.9 | 31.9 |
| 27.6 | 27.1 | 32.0 |
| 28.2 | 27.7 | 33.1 |
| 28.7 | 28.3 | 33.2 |
| 29.1 | 29.0 | 33.5 |
| 30.1 | 30.2 | 34.2 |
| 30.7 | 30.5 | 34.4 |
| 32.0 | 30.7 | 34.9 |
| 33.0 | 31.0 | 35.4 |
| 34.4 | 31.2 | 35.8 |
| 37.0 | 31.9 | 36.2 |
| 37.4 | 32.5 | 36.6 |
|  | 32.6 | 37.2 |
|  | 33.7 | 37.7 |
|  | 34.8 |  |
|  | 35.6 |  |
|  | 35.9 |  |
|  | 36.2 |  |
|  | 36.4 |  |
|  | 36.9 |  |
|  | 37.4 |  |

TABLE 4

Raman spectroscopy bands of crystal forms A, B and C (as defined above)
Band maximum [cm$^{-1}$]

| Crystal form A | Crystal form B | Crystal form C |
|---|---|---|
| 3114 | 3338 | 3302 |
| 3.097 | 3.100 | 3.090 |
| 3.072 | 3.061 | 3.030 |
| 3.032 | 3.035 | 3.016 |
| 2.941 | 3.018 | 2.999 |
| 2.890 | 2.959 | 2.943 |
| 2.878 | 2.915 | 2.919 |
| 2.842 | 2.865 | 2.870 |
| 2.798 | 2.810 | 2.839 |
| 1.700 | 1.686 | 2.812 |
| 1.691 | 1.654 | 1.693 |
| 1.653 | 1.628 | 1.628 |
| 1.639 | 1.604 | 1.617 |
| 1.604 | 1.587 | 1.607 |
| 1.537 | 1.526 | 1.593 |
| 1.513 | 1.478 | 1.576 |
| 1.449 | 1.451 | 1.533 |
| 1.404 | 1.421 | 1.517 |
| 1.382 | 1.393 | 1.480 |
| 1.320 | 1.372 | 1.449 |
| 1.267 | 1.304 | 1.415 |
| 1.250 | 1.262 | 1.404 |
| 1.218 | 1.244 | 1.384 |
| 1.196 | 1.216 | 1.372 |
| 1.160 | 1.206 | 1.303 |
| 1.150 | 1.175 | 1.261 |
| 1.120 | 1.142 | 1.243 |
| 1.101 | 1.112 | 1.215 |
| 1.053 | 1.092 | 1.207 |
| 1.004 | 1.064 | 1.168 |
| 990 | 1.048 | 1.148 |
| 936 | 1.031 | 1.137 |
| 926 | 1.022 | 1.111 |
| 896 | 1.002 | 1.092 |
| 760 | 983 | 1.074 |
| 744 | 938 | 1.048 |
| 697 | 925 | 1.031 |
| 684 | 910 | 1.015 |
| 642 | 904 | 1.002 |
| 598 | 882 | 984 |
| 555 | 864 | 940 |
| 534 | 823 | 924 |
| 500 | 812 | 908 |
| 446 | 786 | 895 |
| 424 | 763 | 883 |
| 362 | 735 | 837 |
| 310 | 713 | 826 |
| 294 | 694 | 788 |
| 263 | 688 | 761 |
| 215 | 649 | 739 |
| 159 | 623 | 710 |
| 103 | 614 | 691 |
| 85 | 594 | 649 |
|  | 580 | 620 |
|  | 555 | 593 |
|  | 512 | 581 |
|  | 464 | 517 |
|  | 445 | 469 |
|  | 421 | 431 |
|  | 394 | 394 |
|  | 356 | 370 |
|  | 345 | 347 |
|  | 254 | 333 |
|  | 218 | 283 |
|  | 186 | 266 |
|  | 147 | 242 |
|  | 133 | 156 |
|  | 98 | 122 |
|  | 84 | 82 |

In a further aspect, the present invention relates to a composition comprising inventive crystal form B in a total amount of at least 5% by weight, wherein this total amount is preferably at least 10, 15, 20, 25, 30, 35, 40, 45, 50, 55, 60, 65, 70, 75, 80, 85, 90, 95% by weight or more, based in each case on the total weight of monosodium salt of foramsulfuron present in the composition.

Such a composition according to the invention is preferably characterized in that the composition comprises inventive crystal form B in a total amount of at least 10% by weight, preferably 15% by weight or more, based in each case on the total amount of monosodium salt of foramsulfuron present in the composition.

A preferred composition according to the invention is thereby characterized in that
it is present in solid form at 25° C. and 1013 mbar,
and/or
the content of monosodium salt of foramsulfuron is 80% by weight or more, preferably 85% by weight or more, preferably 90% by weight or more, particularly preferably 95% by weight or more, based in each case on the total weight of the composition.

A preferred composition according to the invention is characterized in that the composition comprises inventive crystal form B in a total amount of at least 25% by weight, preferably 40% by weight or more, based in each case on the total amount of monosodium salt of foramsulfuron present in the composition, and
the content of monosodium salt of foramsulfuron is 80% by weight or more, preferably 85% by weight or more, based in each case on the total weight of the composition.

A particularly preferred composition according to the invention is characterized in that the composition comprises inventive crystal form B in a total amount of at least 50% by weight, preferably 60% by weight or more, based in each case on the total amount of monosodium salt of foramsulfuron present in the composition,
and
the content of monosodium salt of foramsulfuron is 85% by weight or more, preferably 90% by weight or more, based in each case on the total weight of the composition.

An especially preferred composition according to the invention is characterized in that the composition comprises inventive crystal form B in a total amount of at least 70% by weight, preferably 80% by weight or more, based in each case on the total amount of monosodium salt of foramsulfuron present in the composition,
and
the content of monosodium salt of foramsulfuron is 85% by weight or more, preferably 90% by weight or more, based in each case on the total weight of the composition.

An especially preferred composition according to the invention is characterized in that the composition comprises inventive crystal form B in a total amount of at least 80% by weight, preferably 85% by weight or more, based in each case on the total amount of monosodium salt of foramsulfuron present in the composition,
and
the content of monosodium salt of foramsulfuron is 90% by weight or more, preferably 95% by weight or more, based in each case on the total weight of the composition.

One of the most particularly preferred configurations is a composition according to the invention characterized in that the composition comprises inventive crystal form B in a total amount of at least 90% by weight, preferably 95% by weight or more, based in each case on the total amount of monosodium salt of foramsulfuron present in the composition,
and
the content of monosodium salt of foramsulfuron is 90% by weight or more, preferably 95% by weight or more, based in each case on the total weight of the composition.

In a further aspect, the present invention relates to the use of crystal form B according to the invention or a composition according to the invention as defined above for preparing agrochemical formulations, preferably for preparing herbicidally active agrochemical formulations.

In a further aspect, the present invention relates to the monomethanol solvate of the monosodium salt of foramsulfuron in crystalline form (crystal form C), characterized in that the X-ray powder diffractogram of this salt using Cu Kα radiation at 25° C. has at least 3 of the following 2Θ (2 theta) values:

| 2Θ (2 theta) values in ° |
| --- |
| 9.1 |
| 9.1 |
| 9.7 |
| 12.6 |
| 16.2 |
| 18.5 |

| 2Θ (2 theta) values in ° |
| --- |
| 24.1 |
| 24.3 |
| 24.6 |

The X-ray diffractogram of inventive crystal form C using Cu Kα radiation at 25° C. preferably has at least 4, preferably at least 6, preferably at least 8, more preferably all of the 2Θ (2 theta) values mentioned above.

The X-ray powder diffractogram of inventive crystal form C using Cu Kα radiation at 25° C. more preferably additionally has at least two, four, six, eight, ten, twelve or more, preferably at least 15, 20, 23, 25, 27, 30, 33, 35, 38, 40, 42, 44, 46, 48, 50 or more, preferably all of the following 2Θ (2 theta) values:

| |
| --- |
| 12.0 |
| 14.8 |
| 15.7 |
| 16.3 |
| 17.8 |
| 18.0 |
| 18.2 |
| 19.0 |
| 19.5 |
| 19.9 |
| 20.1 |
| 20.9 |
| 21.1 |
| 21.7 |
| 22.1 |
| 22.6 |
| 23.5 |
| 23.8 |
| 24.5 |
| 25.1 |
| 25.6 |
| 25.8 |
| 26.5 |
| 26.8 |
| 27.1 |
| 28.8 |
| 29.2 |
| 29.7 |
| 30.0 |
| 30.5 |
| 30.8 |
| 31.3 |
| 31.7 |
| 31.9 |
| 32.0 |
| 33.1 |
| 33.2 |
| 33.5 |
| 34.2 |
| 34.4 |
| 34.9 |
| 35.4 |
| 35.8 |
| 36.2 |
| 36.6 |
| 37.2 |
| 37.7 |

Inventive crystal form C is preferably characterized in that the Raman spectrum thereof has at least the following bands:

| Band maximum [cm$^{-1}$] |
| --- |
| 3090 |
| 2943 |
| 2919 |

-continued

| Band maximum [cm$^{-1}$] |
| --- |
| 1593 |
| 1576 |
| 691 |
| 156 |
| 122 |

The Raman spectrum of crystal form C according to the invention preferably has at least ten of the bands specified in Table 4, preferably 15, 20, 25, 30, 35, 40, 45, 50, 55, 60, 65 or more, preferably all of the bands specified in Table 4.

The Raman spectrum of inventive crystal form C preferably corresponds essentially to the spectrum shown in FIG. 6.

The present invention further relates to a composition comprising crystal form C in a total amount of at least 5% by weight, wherein this total amount is preferably at least 10, 15, 20, 25, 30, 35, 40, 45, 50, 55, 60, 65, 70, 75, 80, 85, 90, 95% by weight or more, based in each case on the total amount of monosodium salt of foramsulfuron present in the composition.

The present invention preferably relates to a composition comprising crystal form C (as defined above), wherein
the composition is present in solid form at 25° C. and 1013 mbar,
and/or
the content of monosodium salt of foramsulfuron is 80% by weight or more, wherein the content of monosodium salt of foramsulfuron is preferably 85% by weight or more, preferably 90% by weight or more, particularly preferably 95% by weight or more, based in each case on the total weight of the composition.

Inventive crystal form B can be prepared by the method described below.

The invention further relates to a method for preparing crystal form B comprising the steps of
(a) suspending a monosodium salt of foramsulfuron (preferably of crystal form A), of crystal form C, or a mixture of these substances in a diluent or diluent mixture,
wherein the diluent or diluent mixture used in step (a) is selected from the group consisting of alcohols having 3 to 6 carbon atoms, in this case preferably primary alcohols having 3 to 6 carbon atoms, and ketones having 3 to 6 carbon atoms, and mixtures thereof, or comprises at least 20% by weight thereof, preferably at least 30% by weight, more preferably at least 40% by weight, even more preferably at least 50% by weight thereof.

Crystal form B according to the invention can be obtained if the diluent or diluent mixture used in the method described above comprises 20% by weight or more of alcohols having 3 to 6 carbon atoms and/or ketones having 3 to 6 carbon atoms.

It is preferable if the diluent or diluent mixture used in the method described above comprises 60% by weight or more of alcohols having 3 to 6 carbon atoms and/or ketones having 3 to 6 carbon atoms, since readily filterable crystals are obtained in this manner, which is of considerable advantage in process engineering terms.

The invention therefore relates particularly to a method for preparing crystal form B comprising the steps of
(a) suspending a monosodium salt of foramsulfuron (preferably of crystal form A), of crystal form C, or a mixture of these substances in a diluent or diluent mixture,
wherein the diluent or diluent mixture used in step (a) is selected from the group consisting of alcohols having 3 to 6 carbon atoms, in this case preferably primary alcohols having 3 to 6 carbon atoms, and ketones having 3 to 6 carbon atoms, and mixtures thereof, or comprises at least 60% by weight thereof.

The invention further relates to a method for preparing crystal form B comprising the steps of
(a) suspending foramsulfuron in a diluent or diluent mixture,
(b) reacting foramsulfuron with a base containing sodium, preferably an organic base, in this case preferably sodium methoxide and/or sodium ethoxide,
wherein the diluent or diluent mixture used in step (a) is selected from the group consisting of alcohols having 3 to 6 carbon atoms, in this case preferably primary alcohols having 3 to 6 carbon atoms, and ketones having 3 to 6 carbon atoms, and mixtures thereof, or comprises at least 20% by weight thereof, preferably at least 30% by weight, more preferably at least 40% by weight, even more preferably at least 50% by weight thereof.

The invention relates particularly to a method for preparing crystal form B comprising the steps of
(a) suspending foramsulfuron in a diluent or diluent mixture,
(b) reacting foramsulfuron with an organic base containing sodium, preferably sodium methoxide and/or sodium ethoxide,
wherein the diluent or diluent mixture used in step (a) is selected from the group consisting of alcohols having 3 to 6 carbon atoms, in this case preferably primary alcohols having 3 to 6 carbon atoms, and ketones having 3 to 6 carbon atoms, and mixtures thereof, or comprises at least 60% by weight thereof.

In this case, sodium methoxide in methanol and/or sodium ethoxide in ethanol is preferably used as organic base containing sodium in step (b).

The methods according to the invention for preparing crystal form B are preferably conducted in a manner such that the diluent or diluent mixture used in step (a) is selected from the group consisting of alcohols having 3 to 6 carbon atoms, in this case preferably primary alcohols having 3 to 6 carbon atoms, and ketones having 3 to 6 carbon atoms, and mixtures thereof, or comprises at least 60% by weight thereof, preferably 70% by weight or more, preferably 80% by weight or more, more preferably 90% by weight or more, particularly preferably 95% by weight or more thereof.

The methods according to the invention for preparing crystal form B are preferably conducted in a manner such that the diluent or diluent mixture used in step (a) is selected from the group consisting of 1-butanol, acetone, methyl isobutyl ketone, and mixtures thereof, or comprises 60% by weight or more thereof (preferably 70% by weight or more, preferably 80% by weight or more, more preferably 90% by weight or more, particularly preferably 95% by weight or more thereof).

The methods according to the invention for preparing crystal form B are carried out preferably at temperatures of at least 0° C. The methods according to the invention for preparing crystal form B are preferably carried out at temperatures in the range of 0 to 150° C., preferably at temperatures in the range of 25 to 130° C.

The methods according to the invention for preparing crystal form B are preferably carried out at temperatures of at least 25° C., preferably of at least 30° C., preferably of at least 40° C. The methods according to the invention for preparing crystal form B are preferably carried out at temperatures in the range of 40 to 150° C., preferably at temperatures in the range of 45 to 130° C., particularly preferably in the range of 50 to 120° C.

In particularly preferred methods according to the invention for preparing crystal form B, acetone is used as a diluent or the diluent in step (a). In this case, the methods according to the invention for the preparation are preferably carried out at temperatures in the range of 0 to 65° C., preferably in the range of 25 to 56° C.

In further particularly preferred methods according to the invention for preparing crystal form B, acetone is used as a diluent or the diluent in step (a). In this case, the methods according to the invention for the preparation are preferably carried out at temperatures in the range of 40 to 65° C., preferably in the range of 45 to 56° C., particularly preferably in the range of 50 to 56° C.

The methods according to the invention for preparing crystal form B are preferably carried out in a manner such that the ratio by weight of the total amount of foramsulfuron, crystal form A and crystal form C, to the total amount of diluent or diluent mixture used in step (a) is less than 2:1. The ratio by weight of the total amount of foramsulfuron, monosodium salts of foramsulfuron (preferably crystal form A) and of crystal form C, to the total amount of diluent or diluent mixture used in step (a) is preferably in the range of 3:1 to 1:20, preferably in the range of 2:1 to 1:15, more preferably in the range of 1:1 to 1:10. In many cases, this ratio by weight is preferably in the range of 2:3 to 1:8, and particularly in the range of 1:2 to 1:5.

The method according to the invention for preparing inventive crystal form B preferably comprises further steps, preferably a cooling of the resulting mixture containing crystal form B. In this case, the cooling preferably takes place over a period of at least 15 minutes, preferably of at least 30 minutes.

Here, the cooling more preferably takes place over a period of at least 60 minutes, even more preferably of at least 120 minutes, and particularly preferably of at least 180 minutes.

The method according to the invention for preparing inventive crystal form B preferably comprises further steps, preferably
filtration of the resulting mixture containing crystal form B, and/or
isolation of crystal form B, and/or
drying of crystal form B.

In the context of the method according to the invention for preparing inventive crystal form B, it is preferred if the starting material used, preferably crystal form A and/or crystal form C, is at most sparingly dissolved in the diluent, and in particular—in contrast to recrystallization processes—is not completely dissolved, but rather a solid-solid conversion of the starting material into crystal form B takes place, i.e. a conversion of solid substances.

The invention further relates to a mixture comprising
(i) monosodium salt of foramsulfuron and/or a solvate thereof, preferably comprising crystal form A, crystal form B, crystal form C, or a mixture comprising two or all of these crystal forms, and
(ii) a diluent or diluent mixture selected from the group consisting of alcohols having 3 to 6 carbon atoms, in this case preferably primary alcohols having 3 to 6 carbon atoms, and ketones having 3 to 6 carbon atoms, and mixtures thereof, or comprises at least 20% by weight thereof, preferably at least 30% by weight, more preferably at least 40% by weight, even more preferably at least 50% by weight thereof.

The invention relates particularly to a mixture comprising
(i) monosodium salt of foramsulfuron and/or a solvate thereof, preferably comprising crystal form A, crystal form B, crystal form C, or a mixture comprising two or all of these crystal forms, and
(ii) a diluent or diluent mixture selected from the group consisting of alcohols having 3 to 6 carbon atoms, in this case preferably primary alcohols having 3 to 6 carbon atoms, and ketones having 3 to 6 carbon atoms, and mixtures thereof, or comprises at least 60% by weight thereof, and preferably 70% by weight or more, preferably 80% by weight or more, more preferably 90% by weight or more, particularly preferably 95% by weight or more thereof.

The diluent or diluent mixture is preferably such a mixture according to the invention selected from the group consisting of 1-butanol, acetone, methyl isobutyl ketone, and mixtures thereof, or it comprises at least 60% by weight thereof (preferably 70% by weight or more, preferably 80% by weight or more, more preferably 90% by weight or more, particularly preferably 95% by weight or more thereof).

The ratio by weight of the total amount of constituent (a), monosodium salt of foramsulfuron, to the total amount of constituent (b), diluent or diluent mixture in a mixture according to the invention, preferably corresponds to the weight ratios specified above (as preferred), based in each case on the total weight of the mixture which are stated in connection with the preparation method of inventive crystal form B.

Inventive crystal form B can be employed as such or in the form of agrochemical formulations (formulations) with other pesticidally active ingredients, such as, for example, insecticides, acaricides, nematicides, herbicides, fungicides, safeners, fertilizers and/or growth regulators, for example as finished formulation or as tank mixes. The combination formulations can be prepared on the basis of the formulations mentioned hereinafter, while taking account of the physical properties and stabilities of the active ingredients to be combined. Inventive crystal form B can be formulated in various ways, in which in general customary formulation auxiliaries in the pesticide field are used and/or other (agrochemical) active ingredients.

The invention therefore relates in a further aspect to an agrochemical formulation comprising
(a) a herbicidally effective amount of crystal form B,
and one or more further constituents selected from the group consisting of the following constituents (b-i), (b-ii) and (b-iii):
(b-i) formulation auxiliaries customary in the pesticide field,
(b-ii) further agrochemical active ingredients,
and
(b-iii) crystal form C.

A formulation according to the invention preferably comprises one or more safeners (here preferably isoxadifen, isoxadifen-ethyl and/or cyprosulfamide) as constituent (b-ii) and/or one or more further herbicidal active ingredients.

The further herbicidal active ingredients are preferably selected from the herbicidal active ingredients mentioned in "The Pesticide Manual", 16th edition, The British Crop Protection Council and the Royal Society of Chemistry, 2012. In this case, the preferred herbicidal active ingredients are the herbicidal active ingredients mentioned in EP 0 790 771 A1 or EP 1 104 239 A1, particularly other ALS inhibitors (acetolactate synthase inhibitors), in turn preferably thiencarbazone-methyl and salts thereof and/or other sulphonylurea herbicides, in turn preferably amidosulfuron, mesosulfuron, mesosulfuron-methyl, iodosulfuron, iodosulfuron-methyl, and respective salts thereof such as iodosulfuron-sodium or iodosulfuron-methyl-sodium (the particular advantages with respect to the (stability) improvement in combination with other sulphonylurea herbicides has already been stated earlier).

In addition, the agrochemical formulations (formulations) mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described, inter alia, in "Chemistry and Technology of Agrochemical Formulations", ed. D. A. Knowles, Kluwer Academic Publishers (1998).

Potential useful formulations for inventive agrochemical formulations comprising crystal form B according to the invention include: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

It has also been found that is advantageous, in particular agrochemical formulations according to the invention such as some oil dispersions (OD), to use a mixture of inventive crystal form B and inventive crystal form C. Such agrochemical formulations according to the invention are in this case based preferably on formulations such as are described in US 2002/0016263 A1 or US 2005/0032647 A1.

Such agrochemical formulations comprising a mixture of inventive crystal form B and inventive crystal form C showed, with respect to otherwise identical formulations which contained only crystal form B, further improved properties, for example, a further improved storage stability, particularly in this case with respect to flowability and viscosity of the formulation.

In such agrochemical formulations according to the invention, the ratio by weight of the total amount of crystal form B to the total amount of crystal form C is preferably in the range of 20:1 to 1:10, preferably in the range of 10:1 to 1:5, more preferably in the range of 10:1 to 1:3 and particularly preferably in the range from 5:1 to 1:1, based in each case on the total weight of the agrochemical formulation according to the invention.

These individual formulation types are known in principle and are described, for example, in: Winnacker-Küchler, "Chemische Technologie" [Chemical Technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd ed., Darland Books, Caldwell N.J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Technology], volume 7, C. Hanser Verlag Munich, 4th ed. 1986.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleoylmethyltaurate. To produce the wettable powders, the herbicidally active ingredients are finely ground, for example in customary apparatus such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulphonates such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active ingredient with finely distributed solid substances, for example talc, natural clays such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th ed., McGraw-Hill, New York 1973, pp. 8-57.

Preferred agrochemical formulations according to the invention are those in which the inventive crystal form B is present in solid form. These are, for example, granules, encapsulated granules, tablets, water-dispersible granules, water-dispersible tablets, water-dispersible powders, dust formulations, formulations in which the active ingredient is present in dispersed form, such as, for example: suspension concentrates (SC), oil-based suspension concentrates, suspo-emulsions or suspension concentrates.

Particularly preferred agrochemical formulations according to the invention comprising inventive crystal form B are those in which the agrochemical formulation is present in a form selected from the group consisting of wettable powders (WP), water-soluble powders (SP), suspension concentrates (SC), oil dispersions (OD), capsule suspensions (CS), dusting products (DP), granules for scattering and soil application, granules (GR) in the form of microgranules, spray granules, coated granules and adsorption granules, water-dispersible granules (WG), water-soluble granules (SG), ULV formulations, microcapsules and waxes.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations according to the invention generally comprise 0.1 to 99% by weight, particularly 0.1 to 95% by weight of inventive crystal form B, based on the total weight of the agrochemical formulation, wherein the total amount of inventive crystal form B may be varied depending on the formulations.

In wettable powders, the total amount of inventive crystal form B is typically 10 to 90% by weight, the remainder to 100% by weight consisting of customary formulation constituents.

In emulsifiable concentrates, the total amount of inventive crystal form B may be about 1 to 90% and preferably 5 to 80% by weight. Formulations in the form of dusts generally comprise a total amount of inventive crystal form B of 1 to 30% by weight, preferably 5 to 20% by weight. In water-dispersible granules, the total amount of inventive crystal form B is for example in the range of 1 and 95% by weight, in the range of 10 and 80% by weight, based on the total weight of the agrochemical formulation.

The present invention therefore also provides a method for controlling harmful plants and/or for regulating the growth of plants, characterized in that an effective amount
of crystal form B,
a composition comprising crystal form B, as defined above,
or
an agrochemical formulation according to the invention, as defined above,
is applied to the plants, seeds of plants, the soil in which or on which the plants grow or the area under cultivation.

It has also been found that crystal form B according to the invention, mixtures according to the invention, compositions according to the invention and formulations according to the invention, defined in each case in the context of the present invention, are suitable for controlling harmful plants or for regulating the growth of plants. Controlling of harmful plants or regulating the growth of plants is effected advantageously in particular crop plants. In this case, preferred crop plants are in particular oilseed rape, soya bean, cotton, sugar beet and true grasses, in particular here corn, barley, wheat, rye, oats, triticale, millet, rice, wherein corn is particularly preferred. In a preferred configuration, the crop plants, particularly the crop plants specified as preferred, are transgenic plants.

In addition, application to turf areas, for example golf courses, is also possible.

EXAMPLES

The invention is elucidated by the examples which follow. Unless stated otherwise, all data refer to the weight.

The symbol ">" means "greater than" and the symbol "<" means "less than".

Example 1: Preparation of Crystal Form A 1000 g of N-[(4,6-dimethoxypyridin-2-yl)aminocarbonyl]-2-dimethylaminocarbonyl-5-formylaminobenzenesulphonamide were initially charged in 4750 g of cold 5° C. MeOH (6000 mL).

To this were added 32 g of seed crystals of crystal form A (according to EP 0 757 679 A1) and the mixture cooled to 0° C. over 20 minutes. After reaching a temperature of 0° C., 418 g (440 mL) of 30% sodium methoxide solution were metered in 2 hours, such that an internal temperature of 5° C. was not exceeded.

The resulting very pasty mixture was then divided between two coolable 4 L frits and filtered under suction. After about 2 hours, the filtration was complete and each frit was washed with 500 mL.

In total, 2220 g of moist product were obtained, which were then dried at 65° C. at a pressure <100 mbar. The drying takes 44 h in total. The drying is terminated at a residual methanol content of 1.5% by weight. 1012 g of a 97% strength product were obtained.

Example 2: Variation of Temperature in the Preparation of Crystal Form A in Methanol In separate containers, 20 g of N-[(4,6-dimethoxypyridin-2-yl)aminocarbonyl]-2-dimethylaminocarbonyl-5-formylaminobenzenesulphonamide were each initially charged in 100 g MeOH.

In each case, 1 g of seed crystals of crystal form A was added and one equivalent of NaOMe as a 30% methanolic solution was added at the temperature stated in each case over a period of 2 hours. The post reaction time was 3 hours in each case.

To isolate the respective product, the respective mixture was heated or cooled to 20° C. and then filtered. After drying at 65° C. at a pressure <100 mbar, the residual content of methanol in each product was determined.

| Experiment No. | T in ° C. | Filtration time in s | MeOH content in % by weight |
|---|---|---|---|
| 1 | 0 | 150 | 0.53 |
| 2 | 15 | 50 | 1.49 |
| 3 | 35 | 4 | 2.83 |
| 4 | 50 | 5 | 5.19 |

Example 3: Storage of the Methanol-Moist Crystal Form A and Conversion Thereof into Crystal Form C In separate containers, 5 g each of crystal form A were each stirred with 20 g of MeOH and subsequently filtered off.

At 20° C., 30° C. and 35° C., the moistened products were stored for one week and a sample taken daily. These samples were dried at 65° C. and 100 mbar and the respective methanol content subsequently determined.

Already after 2 days (35° C.), 3 days (30° C.) and 7 days (20° C.), crystal form A had converted practically completely into crystal form C (MeOH content about 6.4% by weight).

Example 4: Preparation of Crystal Form B from Crystal Form A 1000 g of N-[(4,6-dimethoxypyridin-2-yl)aminocarbonyl]-2-dimethylaminocarbonyl-5-formylaminobenzenesulphonamide Na salt (crystal form A) were suspended in 3000 g of acetone and heated under reflux for 2 hours. After cooling to 20° C., the suspension was filtered. The filtration took 60 minutes.

The moist product thus obtained was then dried overnight at 70° C. and a pressure <100 mbar. 9230 g of a 98.6% strength product were obtained. The MeOH content in this product was <0.1% by weight, and the acetone content <0.05% by weight.

Example 5: Preparation of Crystal Form B from Crystal Form C 100 g of N-[(4,6-dimethoxypyridin-2-yl)aminocarbonyl]-2-dimethylaminocarbonyl-5-formylaminobenzenesulphonamide Na salt (crystal form C; MeOH content about 6.4%) were suspended in 300 g of acetone and heated under reflux for 2 hours. After cooling to 20° C., the suspension was filtered. The filtration took a few seconds.

The moist product was dried overnight at 70° C. and a pressure <100 mbar.

92 g of a 99.2% strength product were obtained. The methanol content in this product was below the detection limit, and the acetone content was 0.026% by weight.

Example 6: Preparation of Crystal Form B from Foramsulfuron and Sodium Methoxide 100 g of N-[(4,6-dimethoxypyridin-2-yl)aminocarbonyl]-2-dimethylaminocarbonyl-5-formyl-aminobenzenesulphonamide were suspended in 300 g of acetone and treated with one equivalent of NaOMe as a 30% methanolic solution (40.21 g) at 40° C. over 1 hour. Subsequently, the resulting mixture was heated under reflux for 2 hours. After cooling to 20° C., the suspension was filtered. The filtration took ca. 30 seconds.

The moist product was dried overnight at 70° C. and a pressure <100 mbar.

104 g of a 98.4% strength product were obtained. The methanol content in the product obtained was 0.006% by weight and the acetone content was 0.048% by weight.

Example 7: Preparation of Crystal Form B from Foramsulfuron and Sodium Ethoxide 100 g of N-[(4,6-dimethoxypyridin-2-yl)aminocarbonyl]-2-dimethylaminocarbonyl-5-formylaminobenzenesulphonamide were suspended in 400 g of acetone and treated with one equivalent of NaOEt as a 21% ethanolic solution (73.1 g) under reflux over 1 hour. The mixture was subsequently heated further under reflux for 2 hours. After cooling to 20° C., the suspension was filtered. The filtration took ca. 60 seconds.

The moist product was dried overnight at 70° C. and a pressure <100 mbar.

102 g of a 98.6% strength product were obtained. The ethanol content in the product obtained was 0.0105% by weight and the acetone content was 0.024% by weight.

Example 8: Stability Test of Crystal Form B in Methanol 10 g of crystal form B (MeOH content <0.01%) were suspended in 100 g of methanol and stirred for 7 days at 30° C. The product was filtered and then dried overnight at 70° C. and a pressure <100 mbar.

9.1 g of a 99.4% strength product were obtained. The methanol content in the product obtained was 0.004% by weight and the acetone content was 0.0003% by weight.

Example 9: Investigation of the Chemical Storage Stability of Crystal Forms A and B Crystal forms A and B were each incorporated separately in an otherwise identical formulation in the form of oil dispersions (OD) and stored under the same conditions.

The oil dispersions were stored under the following storage conditions and were analysed with respect to the chemical degradation of crystal form A or B:

Storage for two weeks at 40° C. (specified below as 2 W 40° C.)
Storage for four weeks at 40° C. (specified below as 4 W 40° C.)
Storage for two weeks at 54° C. (specified below as 2 W 54° C.)

In this manner, storage over a longer time period at a correspondingly lower temperature is also simulated.

The crystal forms were incorporated in three different formulations in the form of oil dispersions (OD), where these formulations, in addition to the agrochemical active ingredients specified below, comprised customary formulation constituents such as emulsifiers, thickeners and diluents, and also in some cases pH regulators and/or defoamers.

In addition to 3.05% by weight of crystal form A or B, formulation OD1 comprised as further active ingredients 0.1% by weight iodosulfuron-methyl-sodium (a sulphonylurea herbicide) and 2.91% by weight isoxadifen-ethyl (a safener).

In addition to 3.21% by weight of crystal form A or B, formulation OD2 comprised as further active ingredients 1.02% by weight thiencarbazone-methyl and 1.53% by weight cyprosulfamide (a safener).

In addition to 3.21% by weight of crystal form A or B, formulation OD3 comprised as further active ingredients 0.11% by weight iodosulfuron-methyl-sodium (a sulphonylurea herbicide), 1.02% by weight thiencarbazone-methyl and 1.53% by weight cyprosulfamide (a safener).

TABLE 9-1

Chemical stability of crystal forms A and B in formulation OD 1

| Crystal form | Degradation in % | |
|---|---|---|
| | 4W 40° C. | 2W 54° C. |
| Crystal form A | 3.4 | 7.7 |
| Crystal form B | 1.5 | 3.4 |

TABLE 9-2

Chemical stability of crystal forms A and B in formulation OD 2

|  | Degradation in % | |
|---|---|---|
| Crystal form | 2W 40° C. | 2W 54° C. |
| Crystal form A | 1.8 | 8.6 |
| Crystal form B | 0.6 | 1.8 |

TABLE 9-3

Chemical stability of crystal forms A and B in formulation OD 3

|  | Degradation in % | |
|---|---|---|
| Crystal form | Hardness (40° C.) | 2W 54° C. |
| Crystal form A | 2.1 | 4.8 |
| Crystal form B | 0.3 | 1.4 |

Example 10: Preparation of Crystal Form B from Foramsulfuron and Sodium Methoxide 100 g of N-[(4,6-dimethoxypyridin-2-yl)aminocarbonyl]-2-dimethylaminocarbonyl-5-formylaminobenzenesulphonamide were suspended in 300 g of an acetone/methanol mixture (80:20 parts by weight) and treated with one equivalent of NaOMe as a 30% methanolic solution at 30° C. over 2 hours. Subsequently, the mixture was stirred at 30° C. for another 2 hours. After cooling to 20° C., the suspension was filtered. The filtration took 50 seconds.

The moist product was dried overnight at 70° C. and a pressure <100 mbar.

102 g of a 98.6% strength product were obtained. The methanol content in the product obtained was 0.03% by weight and the acetone content was 0.014% by weight.

Example 11: Preparation of Crystal Form B from Foramsulfuron and Sodium Methoxide 100 g of N-[(4,6-dimethoxypyridin-2-yl)aminocarbonyl]-2-dimethylaminocarbonyl-5-formylaminobenzenesulphonamide were suspended in a mixture of 150 g of acetone and 100 g of methanol and heated to 30° C. To this were added at the same time 38.6 g of NaOMe as a 30% methanolic solution over two hours. Stirring was continued at 30° C. for one hour. The temperature was then increased to 40° C., and after 1 hour at this temperature a further hour at 45° C.

After cooling to 20° C., the suspension was filtered and the filter cake was washed with 100 g of acetone.

The moist product was dried overnight at 70° C. and a pressure <100 mbar.

The methanol content in the product obtained was 0.10% by weight and the acetone content was 0.13% by weight.

Example 12: Sorption/Desorption Curve of Crystal Form B

Sorption and desorption curves of crystal form B were measured isothermically at 25° C.

The sorption curve gives the water uptake at increasing relative humidity and the desorption curve gives the drying behaviour on moisture reduction.

| Relative humidity | Sorption (% by weight) | Desorption (% by weight) |
|---|---|---|
| 10.0% | 0.100 | 0.846 |
| 20.0% | 0.201 | 1.227 |
| 30.0% | 0.313 | 1.495 |
| 40.0% | 0.444 | 1.760 |
| 50.0% | 0.566 | 2.086 |
| 60.0% | 0.684 | 2.269 |
| 70.0% | 0.864 | 2.485 |
| 80.0% | 1.085 | 3.016 |
| 90.0% | 2.335 | 5.151 |

The result of the investigation shows that crystal form B is not hygroscopic.

Example 13: Investigation of the Hygroscopicity of Crystal Forms A, B and C 100 mg each of crystal forms A, B and C were separately filled into small glass vials with snap-on caps. These three glass vials with snap-on caps were placed unsealed in a glass beaker of which the bottom was covered with a small amount of water. The glass beaker was then sealed with a reversible sealing film and stored for one week at 25° C. After this storage period, the water content of the respective sample was determined by Karl Fischer titration. The water content of the sample of crystal form B was 0.4% by weight, and the water content of the samples of crystal forms A and C was 15.7 and 21.3% by weight.

The samples of crystal forms A and C were hygroscopic and after storage were very ductile and sticky whereas the sample of crystal form B was still crystalline and powdery.

The invention claimed is:

1. A monomethanol solvate of the monosodium salt of foramsulfuron in crystalline form, wherein the X-ray powder diffractogram of said salt using Cu Kα radiation at 25° C. has the following 2θ (2 theta) values:

| 2Θ (2 theta) values in ° |
|---|
| 9.1 |
| 9.1 |
| 9.7 |
| 12.6 |
| 16.2 |
| 18.5 |
| 24.1 |
| 24.3 |
| 24.6. |

2. The monomethanol solvate of the monosodium salt of foramsulfuron in crystalline form of claim 1, wherein the X-ray powder diffractogram of said salt using Cu Kα radiation at 25° C. in addition has two or more of the following 2θ (2 theta) values:

| |
|---|
| 12.0 |
| 14.8 |
| 15.7 |
| 16.3 |
| 17.8 |
| 18.0 |
| 18.2 |
| 19.0 |
| 19.5 |
| 19.9 |
| 20.1 |
| 20.9 |

-continued 21.1
21.7
22.1
22.6
23.5
23.8
24.5
25.1
25.6
25.8
26.5
26.8
27.1
28.8
29.2
29.7
30.0
30.5
30.8
31.3
31.7
31.9
32.0
33.1
33.2
33.5
34.2
34.4
34.9
35.4
35.8
36.2
36.6
37.2
37.7.

3. The monomethanol solvate of the monosodium salt of foramsulfuron in crystalline form of claim 2, wherein the X-ray powder diffractogram of said salt using Cu Kα radiation at 25° C. in addition has six or more of the 2θ (2 theta) values recited in claim 2.

4. The monomethanol solvate of the monosodium salt of foramsulfuron in crystalline form of claim 3, wherein the X-ray powder diffractogram of said salt using Cu Kα radiation at 25° C. in addition has twelve or more of the 2θ (2 theta) values recited in claim 2.

5. The monomethanol solvate of the monosodium salt of foramsulfuron in crystalline form of claim 1, wherein the Raman spectrum thereof has at least the following bands:

| Band maximum [cm$^{-1}$] |
| --- |
| 3090 |
| 2943 |
| 2919 |
| 1593 |
| 1576 |
| 691 |
| 156 |
| 122. |

6. A composition comprising monomethanol solvate of the monosodium salt of foramsulfuron in crystalline form of claim 1 in a total amount of at least 5% by weight, based on the total amount of monosodium salt of foramsulfuron present in the composition.

7. The composition according to claim 6, wherein
the composition is present in solid form at 25° C. and 1013 mbar,
and/or
the content of monosodium salt of foramsulfuron is 80% by weight or more, based on the total weight of the composition.

8. The monomethanol solvate of the monosodium salt of foramsulfuron in crystalline form of claim 2, wherein the X-ray powder diffractogram of said salt using Cu Kα radiation at 25° C. in addition has all of the 2θ (2 theta) values recited in claim 2.

\* \* \* \* \*